United States Patent [19]

Bank

[11] Patent Number: 4,894,398
[45] Date of Patent: Jan. 16, 1990

[54] METHOD FOR STABILIZING UNSATURATED ORGANOSILICONE COMPOSITIONS

[75] Inventor: Howard M. Bank, Freeland, Mich.

[73] Assignee: Dow Corning Corporation, Midland, Mich.

[21] Appl. No.: 246,234

[22] Filed: Sep. 19, 1988

Related U.S. Application Data

[62] Division of Ser. No. 120,256, Nov. 13, 1987, Pat. No. 4,798,889.

[51] Int. Cl.$^4$ .............................................. C08K 5/46
[52] U.S. Cl. .......................................... 524/83; 524/86; 524/98; 524/104; 524/236; 524/345; 524/346; 524/347
[58] Field of Search ................. 524/86, 98, 164, 236, 524/345, 346, 347, 83

[56] References Cited

U.S. PATENT DOCUMENTS

| | | | |
|---|---|---|---|
| 2,389,804 | 11/1945 | McGregor et al. | 260/607 |
| 2,389,805 | 11/1945 | McGregor et al. | 260/607 |
| 3,926,909 | 12/1975 | Wei | 260/45.85 |
| 4,384,131 | 5/1983 | Kanner et al. | 556/442 |
| 4,409,290 | 10/1983 | Wise | 428/378 |
| 4,590,231 | 5/1986 | Seltzer | 524/100 |
| 4,722,807 | 2/1988 | Iwahara et al. | 252/404 |
| 4,782,105 | 11/1988 | Ravichandran et al. | 524/236 |
| 4,798,889 | 1/1989 | Plueddemann et al. | 524/236 |

FOREIGN PATENT DOCUMENTS

| | | |
|---|---|---|
| 1248048 | 7/1965 | Fed. Rep. of Germany . |
| 51-19728 | 2/1976 | Japan . |
| 239144 | 6/1967 | U.S.S.R. . |

Primary Examiner—Melvyn I. Marquis
Attorney, Agent, or Firm—Alexander Weitz

[57] ABSTRACT

A method for stabilizing an unsaturated organosilicone is disclosed wherein a stabilizing amount of a hydroxylamine compound is added to the organosilicone to prevent thermal polymerization of the latter. The organosilicone may be an alkoxysilane or an organopolysiloxane having in its molecule a reactive organic group bearing at least one radical selected from acryloxy, methacryloxy, acrylamide, methacrylamide, styryl or vinylbenzyl radicals. The hydroxylamine compound may be added either to the organosilicone or during the preparation of the alkoxysilane from its respective reactants.

19 Claims, No Drawings

METHOD FOR STABILIZING UNSATURATED ORGANOSILICONE COMPOSITIONS

This is a division of Ser. No. 120,256, filed Nov. 13, 1987, now U.S. Pat. No. 4,798,889.

The present invention relates to a method of stabilizing certain organosilicones having terminally unsaturated organo groups. More particularly, the present invention relates to the use of specific hydroxylamines to stabilize such unsaturated alkoxysilanes and polyorganosiloxanes. The present invention also relates to compositions wherein said unsaturated organosilicones contain a stabilizing amount of a hydroxylamine compound.

BACKGROUND OF THE INVENTION

Various organic polymers and monomers often require the addition of stabilizers to protect them from exposure to heat oxidation or light during processing storage or final utility thereof. It is known in the art to employ various hydroxylamines in such applications. Thus, for example in U.S. Pat. No. 3,926,909 Wei teaches the use of dibenzylhydroxylamine and related compounds as stabilizers for spandex and other forms of polyurethanes against discoloration in exposure to combustion fumes, ultraviolet light and smog atmospheres. In such applications it was found that at least one benzyl group in the hydroxylamine must be present.

Selzer et al.. in U.S. Pat. No. 4,590,231 disclose the use of a large number of hydroxylamines as additional stabilizers in polyolefin compositions containing other stabilizers for protection against degradation upon high temperature extrusion, exposure to the combustion products of natural gas, gamma irradiation or upon storage for extended periods.

The use of hydroxylamines is also known as a "shortstop" for terminating free radical polymerizations. Thus, in U.S. Pat. No. 4,409,290 to Wise, diethylhydroxylamine is mentioned as one of many possible shortstop agents for rubbery graft copolymers or overpolymerized copolymers (shell) on a polyacrylate seed (core) which is useful in making glass tire cord adhesives. The adhesives are used to treat glass fiber prior to using the fiber in tire manufacture, wherein the glass fiber has usually been sized with a silane.

A further example of the mention of silanes in connection with hydroxylamines is provided by Kanner in U.S. Pat. No. 4,384,131. In this patent a process of reacting certain aminofunctional silanes with a stoichiometric amount of an oxime or a hydroxylamine in the presence of a catalyst to form an oximatohydridosilane or an aminohydridosilane is disclosed.

Currently, in the art various vinylic alkoxysilanes such as methacryloxy and vinylbenzyl functional trialkoxysilanes are stabilized with compounds such as monomethylether of hydroquinone and 4-tert-butylcatechol, respectively. These stabilizers are ordinarily introduced by way of the organic compounds used in the preparation of the alkoxysilanes in order to prevent thermal polymerization of the unsaturated groups thereon. Some of these stabilizers, such as the two mentioned are activated by oxygen and do not prevent gelation of the alkoxysilane in air-tight containers such as those used in shipping and storage of the product. Moreover, safety considerations often dictate that oxygen levels be kept low during manufacture, storage and use of the alkoxysilanes in view of the potential of fire or explosion.

With this observation in mind, some stabilizers which are not activated by oxygen, such as phenothiazine, have been employed but these can promote gelation in certain alkoxysilanes such as N-beta-(N-vinylbenzylaminoethyl)-gamma-aminopropyltrimethoxysilane hydrochloride. These constraints leave few choices in the selection of adequate stabilizing agents for the alkoxysilanes. Therefore, improved stabilizers, which require little oxygen to maintain their activity, are greatly needed.

SUMMARY OF THE INVENTION

It has now been found that certain hydroxylamines provide such stability to alkoxysilanes and to organopolysiloxanes which contain specific vinylic groups in their molecules. Moreover, this stability is imparted without the need for continued activation by oxygen, permitting the storage of these materials in sealed containers. The present invention, therefore, relates to a method for stabilizing an organosilicone, selected from the group consisting of alkoxysilanes and organopolysiloxanes, having in its molecule a reactive organic group bearing at least one radical selected from the group consisting of acryloxy, methacryloxy, acrylamide, methacrylamide, styryl and vinylbenzyl radicals, said method comprising adding to said organosilicone a stabilizing amount of a hydroxylamine compound selected from the group consisting of those having the general formula

in which Q independently denotes an alkyl radical having 1 to 12 carbon atoms, a cycloalkyl group having 5 to 12 carbon atoms or an aryl group having 6 to 9 carbon atoms and those having the formula

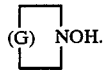

in which G denotes a hydrocarbyl group having 5 to 11 carbon atoms.

The present invention further relates to a method for preparing an alkoxysilane in the presence of a polymerization stabilizer, said alkoxyoilane having a functional moiety selected from the group consisting of acryloxy, methacryloxy, acrylamide, methacrylamide, styryl and vinylbenzyl radicals attached thereto, the improvement comprising using as said stabilizer a stabilizing amount of the above described hydroxylamine compound.

The present invention still further relates to compositions comprising the above described alkoxysilanes or organopolysiloxanes which contain a stabilizing amount of the hydroxylamine compound.

DETAILED DESCRIPTION OF THE INVENTION

This invention relates to a method for stabilizing an organosilicone selected from alkoxysilanes or organopoly-siloxanes, having a functional moiety selected from the group consisting of acryloxy methacryloxy, acrylamide, methacrylamide, styryl and vinylbenzyl radicals in its molecule. In the method of the present invention, a stabilizing amount of a hydroxylamine compound is added to the above organosilicone to reduce the thermal polymerization tendencies of the latter.

The hydroxylamine compound of the present invention may be selected from those having the general structure

Q₂NOH, in which Q independently denotes an alkyl radical having 1 to 12 carbon atoms, a cycloalkyl group having 5 to 12 carbon atoms or an aryl group having 6 to 9 carbon atoms. Examples of specific alkyl groups which are suitable include methyl, ethyl, propyl, isopropyl, butyl, ethylhexyl, nonyl, decyl and dodecyl radicals. Specific cycloalkyl groups include cyclopentyl, cyclohexyl, and cyclooctyl radicals. Illustrative of the aryl groups are the phenyl, benzyl, styryl, tolyl and xenyl radicals. For the purposes of the present invention, the Q groups may be mixed so that hydroxylamine compounds such as ethylbenzylhydroxylamine, ethylcylopentylhydroxylamine, ethylmethylhydroxylamine, and the like, are contemplated herein.

Alternatively, the hydroxylamine compound may be selected from those having the general formula

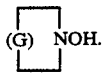

in which G denotes a hydrocarbyl group having 5 to 11 carbon atoms. It is preferred that G be the group —(CH₂)ⱼ— in which j is 5 to 8. Preferably j is 5.

The hydroxylamine compounds of the present invention are well known in the art and may generally be prepared by reacting hydroxylamine or a substituted hydroxylamine with an activated halogen compound in the presence of an acid acceptor or by oxidizing an amine with a peroxy compound such as hydrogen peroxide followed by reduction of the oxyl intermediate formed. Alternatively, the oxime of a cyclic ketone may be reduced to the corresponding hydroxylamine.

For the purposes of the present invention, it is preferred that the hydroxylamine compound be selected from diethylhydroxylamine or dibenzylhydroxylamine, the diethylhydroxylamine being most preferred.

The method of the present invention is generally applicable to any alkoxysilane or organopolysiloxane having in its molecule a reactive organic group (Z) bearing at least one unsaturated (vinylic) radical selected from acryloxy, methacryloxy, acrylamide, methacrylamide, styryl or vinylbenzyl radicals. For the purposes of the present invention, these radicals are defined by the following general structures:

| Acryloxy | —O—C(O)CH=CH₂ |
| Methacryloxy | —O—C(O)C(Me)=CH₂ |
| Acrylamide | —N—C(O)CH=CH₂ |
|  | \| |
| Methacrylamide | —N—C(O)C(Me)=CH₂ |
|  | \| |
| Styryl | —(C₆H₄)—CH=CH₂ and |
| Vinylbenzyl | —CH₂—(C₆H₄)—CH=CH₂, | wherein Me hereinafter denotes the methyl radical.

The exact nature of the remaining portion of the Z group is not critical, but it must exclude functionality which would react with the unsaturated radical on Z. In other words, this portion of the Z group serves only as a connecting group to link the vinylic functionality of Z with the main body of the alkoxysilane (or organopolysiloxane) and is preferably chemically non-reactive. Thus, for example this portion of Z may be a divalent connecting group such as a hydrocarbon group or an arylene connecting group. The connecting group of Z may further comprise such atoms as oxygen, nitrogen, halogen and phosphorous.

One class of alkoxysilanes which is advantageously stabilized by the method of the present invention may be represented by the general formula

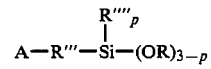

wherein A is selected from acryloxy, methacryloxy, acrylamide or methacrylamide groups. Preferably, A is the methacryloxy group. In the above formula, R''' is a divalent hydrocarbon radical having 1 to 11 carbon atoms. Alkylene groups such as methylene, ethylene, propylene, isopropylene, butylene, isobutylene, 2-ethylhexylene, decylene and octylene are specific examples of R'''. Alternatively, R''' may be an aryl-containing alkylene group such as —CH₂CH₂—(C₆H₄)—CH₂—, The group R'''' is selected from alkyl radicals having 1–6 carbon atoms or the phenyl radical, and is preferably methyl. Further, R is an alkyl or alkoxyalkyl group having 1 to 6 carbon atoms, such as methyl, ethyl, propyl methoxyethyl and ethoxyethyl. Preferably R is methyl. The value of p is 0, 1 or 2.

Specific examples of alkoxysilanes containing acryloxy or methacryloxy groups include 3-methacryloxypropyltrimethoxysilane, 3-methacryloxypropyldimethylethoxysilane, 3-methacryloxypropylmethyldiethoxysilane, 3-acryloxypropyltrimethoxysilane, the structure (MeO)₃SiCH₂CH₂—(CH₆H₄)—CH₂OC(O)C(Me)=CH₂ and methacryloxypropenyltrimethoxysilane. Specific acrylamide compounds include such structures as

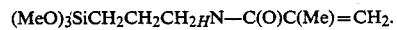

wherein the hydrogen on nitrogen is not substituted, and structures in which this hydrogen is substituted, such as

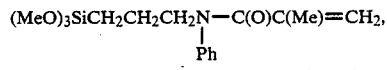

in which Ph hereinafter denotes the phenyl group. Of these, 3-methacryloxypropyltrimethoxysilane represents a preferred embodiment in the present invention.

Another group of alkoxysilane amenable to the method of the present invention may be represented by the general formula

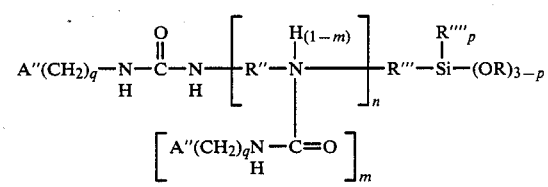

wherein A″ is selected from the group consisting of acryloxy and methacryloxy radicals. Preferably A is methacryloxy. R″ is a divalent hydrocarbon radical having 2 to 4 carbon atoms. such as ethylene, propylene or butylene, preferably ethylene. In this formula, q is 2, 3, or 4 n is 0, 1 or 2, and m has an average value from 0 to 1.0 when n is at least 1. the other symbols having their previously defined meanings.

These alkoxysilanes may be prepared by reacting an isocyanato alkyl ester with an aminoorganosilane according to methods described by Plueddemann in U.S. Pat. No. 4,650.889. assigned to the assignee of the present invention and hereby incorporated by reference. The molar ratio of isocyanatoalkyl ester to said aminoorganosilane may be varied from 1.0 to (1+n) within the scope of this invention to yield the silane having the above formula. Reaction between the isocyanatoalkyl ester and the aminoorganosilane is facile and usually complete within ten minutes at 25° C. so that heating is not necessary.

When preferred aminoorganosilane, N-beta-aminoethyl gamma-aminopropyltrimethoxysilane, is reacted with preferred isocyanatoalkyl ester. 2-isocyanatoethyl methacrylate (IEM). the resulting alkoxysilanes are water dispersible or soluble when the molar ratio of IEM to N-beta-aminoethyl-gamma-aminopropyltrimethoxysilane is in the range of 1.0 to 1.75. The water dispersions of the alkoxysilanes represent a commercially desirable embodiment for use as coupling agents, and a value of about 1.5 to 2 for the molar ratio of IEM to N-beta-aminoethyl-gammaaminopropyltrimethoxyisilane is most preferred. Thus, a preferred embodiment of these alkoxysilanes is

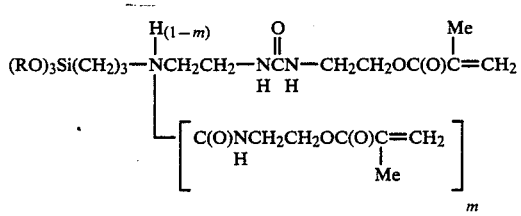

wherein (RO) represents mixed alkoxy groups —OMe and —OPr, in which Pr represents isopropyl radical and m is 0.5 to 1.0. It is most preferred that m=0.5. This mixture results from group exchange during the preferred method of preparation, described in the Examples section, infra.

Yet another category of alkoxysilanes contemplated herein may be represented by the general formula

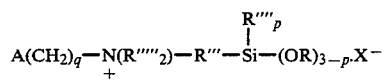

wherein R″″″ denotes hydrogen, the methyl radical or the phenyl radical, $X_{13}$ represents chloride or bromide ion and the other symbols have their previously defined meanings.

These compounds are well known in the art and may be prepared by methods outlined by Plueddemann in U.S. Pat. No. 3,734,763, assigned to the assignee of the present invention and hereby incorporated by reference.

Particularly preferred structures of such cationic organosilanes for the purposes of the present invention include 2-methacryloxyethyldimethyl-(3-trimethoxysilylpropyl) ammonium chloride and 3-methamidopropyldimethyl-(3trimethoxysilylpropyl) ammonium chloride the latter having the structure

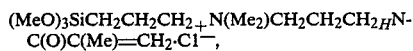

the former being highly preferred.

Another class of organosilanes which benefit from the method of the present invention may be represented by the general formula

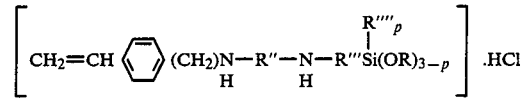

wherein the symbols have their previously defined meanings.

These vinylbenzyl functional alkoxysilanes are well known in the art and can be prepared by methods disclosed by Plueddemann in U.S. Pat. No. 3,734,763, cited supra. At least one such compound is available commercially, namely the preferred N-beta-(N-vinylbenzylaminoethyl)-gamma-aminopropyltrimethoxysilane hydrochloride. It has also been found that, when this preferred alkoxysilane is neutralized (e.g. with NaOH) to form the respective free amine, this neutralized alkoxysilane is also effectively stabilized with the hydroxylamines of the present invention and represents another preferred embodiment.

Additional examples of the alkoxysilanes contemplated in the present invention, but not specifically embraced by the above general structures, include acrylamides and methacrylamides such as

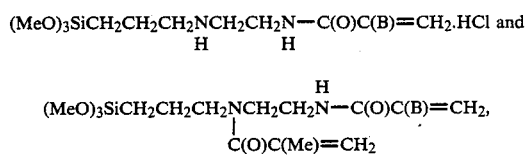

wherein B denotes H or Me, and the reaction products of $(MeO)_3SiCH_2CH_2CH_2NCH_2CH_2NCH_2CH_2NH_2\ +$
                                H                 H $3[O(C(O)C(Me)=CH_2)_2]$, $(MeO)_3SiCH_2CH_2CH_2C(Me_2)CH_2NH_2\ +$ $[O(C(O)C(Me)=CH_2)_2]$ and

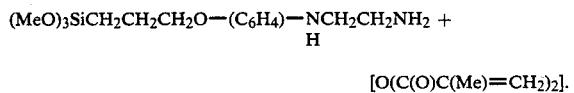

$[O(C(O)C(Me)=CH_2)_2]$.

Further examples of styryl and vinylbenzyl functional alkoxysilanes include the structures $CH_2=CH-(C_6H_4)-CH(Me)Si(OMe)_3$ and $CH_2=CH-(C_6H_4)CH_2CH_2Si(OMe)_3$ which may be prepared according to methods disclosed by Plueddemann in U.S. Pat. No. 3,079,361 assigned to the assignee of the present invention and hereby incorporated by reference.

Furthermore, alkoxysilanes having the styryl group attached directly to silicon are contemplated herein. An example of such a compound is $CH_2=CH-(C_6H_4)-Si(OMe)_3$, which compound may be made by methoxylating styryltrichlorosilane. Styryltrichlorosilane, in turn, may be prepared by passing an equimolar mixture of chlorostyrene and trichlorosilane through a quartz tube heated to 640°–660° C. for a contact time of about 1 second and subsequently distilling the product.

Other examples of acrylate functional alkoxysilanes suitably employed in the instant method are Michael addition products of trimethylolpropane triacrylate and an aminoorganoalkoxysilane. which provide structures such as $(MeO)_3Si(CH_2)_3\nu NCH_2CH_2NV_2$ and $(MeO)_3Si(CH_2)_3\nu NCH_2CH_2\nu NH$ in which V is the group

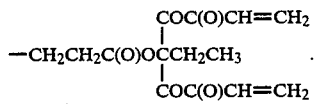

The organopolysiloxanes which may be stabilized with the hydroxylamine compounds of the present invention also contain acryloxy, methacryloxy, acrylamide, methacrylamide, styryl or vinylbenzyl groups in their molecules. These materials are well known in the art and specific examples of such organopoly-siloxanes bearing acryl-type functionality have been described as component (ii) by Lo and Ziemelis in U.S. Pat. No. 4,698,406 assigned to the assignee of the present invention and hereby incorporated by reference.

The organopolysiloxanes contemplated herein comprise a plurality of organosiloxane units of the general formula

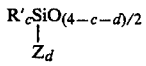

wherein Z is a reactive organic group bearing at least one group selected from acryloxy, methacryloxy, acrylamide, methacrylamide, styryl or vinylbenzyl radicals. In the above formula, R' is a non-reactive group which may be independently selected from alkyl radicals having 1-6 carbon atoms such as methyl, ethyl, propyl, butyl, isopropyl and hexyl radicals. The R' group may also be selected from monovalent cycloaliphatic radicals, such as cyclopentyl, cyclohexyl, or cyclooctyl radicals. Alternatively, R' can be an aryl group such as phenyl, benzyl, styryl, tolyl and xenyl. Still further, R' may be a monovalent halohydrocarbyl group having 1 to 6 carbon atoms such as 3,3,3-trifluoropropyl. 3-chloropropyl and perfluorobutylethyl. Finally, R' may be a monovalent haloaromatic group such as 2,4-dichlorophenyl. It is preferred that R' is selected from methyl, phenyl or 3,3,3-trifluoropropyl radicals. On average, when the above organopolysiloxane contains at least one reactive Z group per molecule, it is considered to be within the scope of the present invention. In any given organosiloxane unit, the value of c may be 0, 1, 2 or 3, the value of d may be 0,1 or 2 and the sum (c+d) is less than 4.

Non-reactive units (i.e., those which do not contain reactive groups Z) of the organopolysiloxane may be composed of any combination of siloxane units of the formulae $R'_3SiO_\frac{1}{2}$, $R'_2SiO_{2/2}$, $R'SiO_{3/2}$, and $SiO_{4/2}$, bonded together by Si-O-Si bonds. Examples of suitable non-reactive siloxane units are endblocking triorganosiloxane units, such as $Me_3SiO_\frac{1}{2}$, $PhMe_2SiO_\frac{1}{2}$, $CF_3CF_2CF_2CF_2CH_2CH_2Me_2SiO_\frac{1}{2}$. $CF_3CH_2CH_3Me_2SiO_\frac{1}{2}$ and $Ph_2MeSiO_\frac{1}{2}$; backbone diorganosiloxane units such as $Me_2Si_{2/2}$, $PhMeSiO_{2/2}$ $CF_3CH_2CH_2MeSi_{2/2}$. $Ph_2SiO_{2/2}$, $ClCH_2CH_2CH_2Si_{2/2}$ and $CF_3CF_2CF_2CF_2CH_2CH_2MeSi_{2/2}$; and branching monoorganosiloxane units, such as $MeSi_{3/2}$, $PhSiO_{3/2}$ and $SiO_{4/2}$.

Preferred organopolysiloxanes are selected from linear copolymers having an average structure which may be represented by the formulae

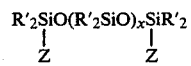

or

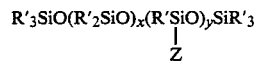

wherein R' is independently selected from the non-reactive radicals defined above, the average value of x may vary from 0 to about 100 and the average value of y may vary from 1 to about 30. Lower molecular weight polydimethylsiloxanes derive the most benefit from the method of the present invention. While not wishing to be bound by any theory or mechanism, it is believed that stabilization of the vinylic functionality becomes less necessary as its concentration in the polyorganosiloxane is reduced at higher molecular weights. Those skilled in the art will readily determine the particular hydroxylamine compound, and in what quantity, is optimally incorporated in a given polyorganosiloxane, by routine experimentation based on the instant disclosure.

For the purposes of the present invention, it is preferred that the Z group contains acryloxy methacryloxy, acrylamide or methacrylamide functionality. Preferred acrylamide structures may be represented by the formulae

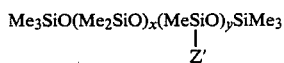

or

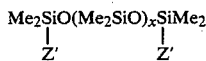

wherein Me denotes the methyl radical and Z' is selected from

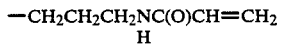

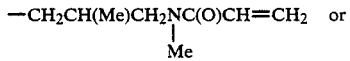

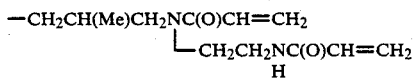

groups, x is less than about 70 and y is 2 to 4. The latter Z' group is preferred. These materials are well known in the art and may be prepared by methods outlined by Varaprath in U.S. Pat. No. 4,608,270, assigned to the assignee of the present invention and hereby incorporated by reference.

In one aspect, the method of the present invention is carried out by simply forming a homogeneous mixture of the hydroxylamine compound with an alkoxysilane or organopolysiloxane of the present invention. Any ordinary mixing method may be utilized, the method and equipment being dictated mainly by the viscosity of the organosilicone. In the case of the low viscosity alkoxysilanes, a low shear mixer such as a blade mixer may be used. For higher viscosity siloxane polymers, a high shear mixer such as a roll mill or sigma-blade mixer may be required to obtain uniform dispersion of the stabilizer.

The exact amount of hydroxylamine compound to be used in the method of the present invention will greatly depend upon the desired degree of stability, the particular alkoxysilane or polyorganosiloxane selected and, of course, the structure of the hydroxylamine compound. Those skilled in the art will readily determine the appropriate amount of hydroxylamine compound to be added to stabilize a given organosilicone by routine experimentation. In this connection, it will be recognized that the upper limit of hydroxylamine compound to be added according to this disclosure is obviously selected so as not to interfere with the intended use of the alkoxysilane or organopolysiloxane. For example, it is possible to add so much stabilizer that subsequent free-radical polymerization, even though desired, would become difficult.

By way of illustration, it has been found that when the highly preferred diethylhydroxylamine is selected, from about 0.04 to 1.0 parts by weight per 100 parts by weight of 3-methacryloxypropyltrimethoxysilane provides satisfactory stability at 145° C. to this alkoxysilane.

Similarly, from about 0.18 parts by weight of diethylhydroxylamine per 100 parts by weight of

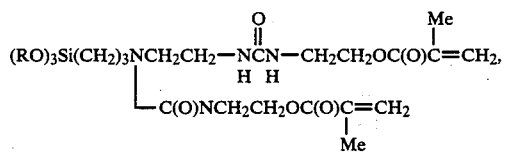

wherein (RO) represents mixed alkoxy groups —OMe and —OPr, in which Pr denotes the isopropyl radical, provides satisfactory stability to this alkoxysilane at 50° C.

Likewise, from about 0.09 to 1.0 parts by weight of diethylhydroxylamine per 100 parts by weight of 2-methacryloxyethyldimethyl-(3-trimethoxysilylpropyl) ammonium chloride provides satisfactory stability to this alkoxysilane at 50° C.

In the same manner, from about 0.08 to 0.8 parts by weight of diethylhydroxylamine per 100 parts by weight of N-beta-(N-vinylbenzylaminoethyl)-gamma-aminopropyltrimethoxysilane hydrochloride provides satisfactory stability to this alkoxysilane at 50° C.

In another aspect of the method of the present invention, the above described hydroxylamine compound may be employed as a stabilizer in the preparation of the alkoxysilanes from their respective reactants. In this case, the hydroxylamine compound is added with the reactants and is present during the formation of the alkoxysilane, thereby protecting the vinylic groups, borne by at least one of said reactants, from thermal polymerization. This procedure is considered particularly suitable with respect to the preparation of N-beta-(N-vinylbenzylaminoethyl)-gamma-aminopropyltrimethoxysilane hydrochloride from N-(beta-aminoethyl)-gamma-aminopropyltrimethoxysilane and vinyl-benzyl-chloride wherein about 0.08 to 0.8 parts by weight of diethylhydroxylamine is added to 100 parts of the total weight of the reactants (on a solids basis).

Similarly, about 1.0 part by weight of diethylhydroxylamine is added to 100 parts by weight (solids basis) of a mixture of 3-chloropropyltrimethoxysilane and 2-(dimethylamino)ethyl methacrylate to provide a storage-stable 2-methacryloxyethyldimethyl-(3-trimethoxysilylpropyl) ammonium chloride. Adding the diethylhydroxylamine during the reaction in this preparation results in yellowing of the product alkoxysilane and it is therefore preferred to add this particular stabilizer to the finished product. In general, whether the hydroxylamine compound is added before or after reaction is a matter to be determined by routine experimentation by those skilled in the art.

The present invention also relates to a composition comprising the organosilicone and the hydroxylamine compound in the above described methods. Although the hydroxylamine compounds contemplated in the present invention provide excellent thermal stability to the above described alkoxysilanes and polyorganosiloxanes, it may be desirable to include other stabilizers in these compositions to further augment their stability. Additional stabilizers, which may be used in conjunction with the hydroxylamine compounds of the present invention, may be selected from free-radical inhibitors which require oxygen to maintain their activity, such as monomethylether of hydroquinone (MEHQ), 4-tert-butylcatechol, 2,6-dibutyl-4-methylphenol, hydroquinone butylated hydroxytoluene, p-aminophenol, cupric chloride, cupric acetate, methylene blue, and the like. Likewise, inhibitors which do not rely on the presence of oxygen may be added to the compositions of the present invention and include such compounds as phenothiazine (PTZ) diphenylphenylenediamine (DPPD), di-beta-napthyl-para-phenylenediamine and a mixture of 2.6-di-tert-butyl-p-cresol with phenothiazine.

The method of the present invention finds utility by inhibiting thermally induced gelation and viscosity drift of the above described alkoxysilanes and polyorganosiloxanes. The method disclosed herein may be advantageously utilized to provide storage-stable compositions which can withstand temperature extremes during storage in closed containers, particularly during the summer months. In the case of alkoxysilanes having a sufficiently low molecular weight (e.g., 3-methacryloxypropyltrimethoxysilane). the method may be used to stabilize these compounds during distillation. As discussed above, the method of the present invention may also be employed wherein the hydroxylamine compound is added to the reactants during the preparation of the alkoxysilane. It is thus possible to reduce the need for oxygen and its associated hazards during such reactions relative to one in which an oxygen-activated free-radical inhibitor is used.

EXAMPLES

The following examples are presented to further illustrate the method and compositions of this invention, but are not to be construed as limiting the invention, which is delineated in the appended claims. All parts and percentages in the examples are on a weight basis unless indicated to the contrary.

Examples 1–4

Two lots of a commercial cationic alkoxysilane consisting essentially of a 40% by weight solution in methanol of N-beta-(N-vinylbenzylaminoethyl)-gamma-aminopropyltrimethoxysilane hydrochloride (Z -6032: Dow Corning Corporation. Midland. MI) were tested for stability at 50° C. (Comparative Examples 2 and 4). The test consisted of filling ½ ounce vials with approximately 18 grams of the organosilane solution leaving about a ½ inch high void space at the top of each vial. In filling the vials, no attempt was made to exclude ambient air. The vials were tightly sealed with screw caps to prevent any further ingress of air or moisture from the atmosphere and placed in an air oven for the times indicated in Table 1. Initial viscosities of the 40% solutions, and their viscosities after the indicated storage times at 50° C., are shown in Table 1. The same alkoxysilane lots containing diethylhydroxylamine, reported on a solids basis in Examples 1, and 3 of Table 1, were similarly tested.

TABLE 1

Stability of Two Lots of N—beta-(N-vinylbenzylaminoethyl)-gamma aminopropyltrimethoxysilane hydrochloride

| Example | Silane Lot | Parts Diethyl-hydroxylamine per 100 Parts Silane | Initial Viscosity (cS at 25° C.) | Storage at (50° C. (Days) | Viscosity After Storage (cS at 25° C.) |
|---|---|---|---|---|---|
| Example 1 (Comparative) | A | 0.089 | 2.73 | 62 | 2.99 |
| Example 2 | A | 0 | 2.73 | 7 | Gel |
| Example 3 (Comparative) | B | 0.84 | 2.58 | 34 | 2.59 |
| Example 4 | B | 0 | 2.58 | 14 | Gel |

TABLE 2

Stability of Gamma-Methacryloxypropyltrimethoxysilane

| Example | Parts Diethyl-hydroxylamine per 100 Parts Silane | MEHQ Content (PPM)* | Gel Time at 145° C. +/− 5° C. |
|---|---|---|---|
| Example 5 | 0.060 | <1 | 12 days |
| Example 6 (Comparative) | 0.048 | <1 | >8 days but <11 days |
| Example 7 (Comparative) | 0.0020 | <1 | 1 hour |
| Example 8 | 0 | <1 | 30 minutes |
| Example 9 | 1.0 | 12 | >35 days |
| Example 10 | 0.34 | 12 | 19 days |
| Example 11 (Comparative) | 0.1 | 12 | 12 days |
| Example 12 | 0 | 12 | 2 hours |
| Example 13 | 0.063 | 30 | 9 days |
| Example 14 (Comparative) | 0.0028 | 30 | 1 hour |
| Example 15 | 0 | 30 | 1 hour |

*MEHQ = Monomethylether of Hydroquinone

From Table 2, it can be seen that the addition of a sufficient amount of the diethyhydroxylamine significantly increased the gel time of the gamma-methacryloxypropyltrimethoxysilane in the presence of monomethylether of hydroquinone versus the comparative examples. This increase of stability was also observed in the absence of such additional stabilizers, as seen from the extended gel times of Examples 5 and 6.

It is apparent from Table 1 that the viscosities of the compositions of the present invention changed little during storage at elevated temperature while the unmodified alkoxysilane solutions gelled.

Furthermore, the composition of Example 3 was used to treat glass cloth which was made into a low-temperature cure unsaturated polyester laminate. No discernible performance difference was observed versus such laminates prepared with glass cloth treated with unmodified N-beta-(N-vinylbenzylaminoethyl)-gamma-aminopropyl-trimethoxysilane hydrochloride.

Examples 5–15

Gamma-methacryloxypropyltrimethoxysilane which originally contained 30 ppm of the stabilizer monomethylether of hydroquinone (MEHQ), was distilled under vacuum to provide gamma-methacryloxypropyltrimethoxysilane samples which contained from 30 ppm of the MEHQ down to non-detectable levels of MEHQ (i.e., less than 1 ppm), as indicated in Table 2. Samples containing varying amounts of diethylhydroxylamine were tested for stability according to the method outlined in Examples 1–4. except that the vials were heated to 145° C. ±/−5° C. in an oil bath.

Examples 16–17

A 3-neck flask equipped with a stirrer a thermometer and a condenser was purged with a 2% (by volume) oxygen in nitrogen gas mixture. There was then added 811.7 g of isopropyl alcohol and 444 g (2 moles) of distilled N-beta- aminoethyl-gamma-aminopropyltrimethoxysilane. Purging with the above gas mixture was continued and, while stirring rapidly 620.6 g (4 moles) of 2-isocyanatoethyl methacrylate (IEM). Experimental Monomer XAS 10743.00, (Dow Chemical Co. Midland, Mich.) was added over a period of 75 minutes. During this time, the reaction temperature was maintained at 50° C. An additional 252.9 g of isopropyl alcohol was then added to provide a total solids content of 50%. At this point, infrared analysis showed no remaining isocyanate functionality in the reaction mixture. A total of 2116.9 g of a clear, slightly yellow liquid was recovered, which liquid had an amine neutral equivalent of 12,500, refractive index of 1.4328, specific gravity of 0.937 and a viscosity of 13.35 cS, the last three determinations being made at 25° C. Based on silicon-29 NMR, carbon-13 NMR and infrared analyses, the average structure of the alkoxysilane so prepared was believed to be

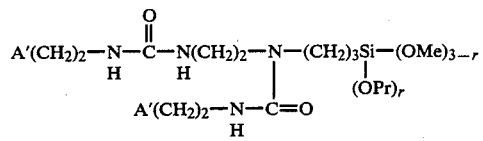

wherein A' is the methacryloxy radical and Me and Pr denote the methyl and isopropyl radicals, respectively. In the above formula, r had an average value of about 0.15, showing that alkoxy group exchange had occurred between the methoxysilane and the isopropyl alcohol.

When the above solution was stored at room temperature in a capped glass bottle, it gelled in less than 2.5 months. However, when the solution was stored in a low density polyethylene bottle for 447 days the viscosity increased to only 15.35 cS at 25° C. It was believed that, in the first case depletion of oxygen resulted in deactivation of the stabilizer supplied with the IEM reactant, while storage in an oxygen-permeable container resulted in continued activity of the stabilizer (2.6-dibutyl-4methylphenol).

The solution which was stored in the polyethylene bottle and had a viscosity of 15.35 cS at 25° C., was tested according to the method described in Examples 1–4. After storage at 50° C. for 3 days, this material formed a gel (Comparative Example 17). When 0.18 part of diethylhydroxylamine was added per 100 parts of the alkoxysilane (based on solids), storage for 71 days at 50° C. resulted in a viscosity increase to only 20.33 cS at 25° C. (Example 16), again indicating an improvement in stability in a closed container.

Examples 18–20

A quaternary ammonium-functional alkoxysilane having the structure

A'(CH$_2$)$_2$—N(Me)$_2$—(CH$_2$)$_3$Si(OMe)$_3$ Cl—, wherein A' is the methacryloxy radical and Me denotes the methyl radical, was prepared from 3-chloropropyl-trimethoxysilane and 2-(dimethylamino)ethyl methacrylate (the latter containing about 2.000 ppm of the stabilizer MEHQ) according to a method described in U.S. Pat. No. 3,734,763 to Plueddemann cited supra. The reaction was conducted in propylene carbonate solvent at 60% solids.

The above solution of 2-methacryloxyethyldimethyl(3-trimethoxysilylpropyl) ammonium chloride was mixed with diethylhydroxylamine in the amounts (solids basis) indicated in Table 3 and tested according to the methods of Examples 1–4.

diethylhydroxylamine was included (Examples 18 and 19) versus the control alkoxysilane, which contained no diethylhydroxylamine (Comparative Example 20).

Examples 21–22

A 70% solution of 2-methacryloxyethyldimethyl(3-trimethoxysilylpropyl) ammonium chloride in propylene carbonate was prepared as in Examples 18–20. In this case, however. diethylhydroxylamine and the stabilizer phenothiazine (PTZ) were added at the start of the reaction. It was calculated that the final solution contained 0.09 parts of PTZ and 0.94 parts of diethylhydroxylamine each based on 100 parts of the 2-methacryloxyethyldimethyl(3-, trimethoxysilylpropyl) ammonium chloride product solids (Example 21). The resulting solution. which had an initial viscosity of 72.6 cS at 25° C. was again tested for stability at room temperature. After 89 days the viscosity had risen to only 91.0 cS at 25° C.

The above preparation was repeated wherein the diethylhydroxylamine was not included with the reactants. The resulting solution, which had an initial viscosity of 51.3 cS at 25° C., was tested at room temperature, as above, and gelled within 4 days (Comparative Example 22).

These examples indicate that the diethylhydroxylamine was also an effective stabilizer when incorporated during the formation of 2-methacryloxyethyldimethyl(3-trimethoxysilylpropyl) ammonium chloride. Examples 23–24

A nitrogen-purged flask was charged with 34.0 g of dimethylaminopropyl methacrylamide containing 600 ppm of the stabilizer MEHQ, 43.67 g gamma-chloropropyltrimethoxysilane, 51.78 g of propylene carbonate solvent and 4 drops of diethylhydroxylamine. The mixture, which contained 60% solids, was heated under an oxygen-free nitrogen blanket for about 3 hours at 123°–126° C. The product acrylamide solution had a viscosity of 116.87 cS at 25° C. and was still fluid after storage in a closed container for a period greater than one year (Example 23).

The above preparation was repeated wherein the diethylhydroxylamine was not included during the reaction. This solution gelled during the reaction in about 5.5 hours at a temperature of 110° C (Comparative Example 24).

Examples 25–28

The following acrylamide functional polydimethylsiloxanes were prepared according to methods described by Varaprath in U.S. Pat. No. 4,608,270, cited supra:

TABLE 3

| Stability of 2-Methacryloxyethyldimethyl(3-trimethoxysilylpropyl) Ammonium Chloride | | | | |
|---|---|---|---|---|
| Example | Parts Diethyl-hydroxylamine per 100 Parts Silane | Initial Viscosity (cS at 25° C.) | Storage Time (Days) | Storage Temperature (°C.) | Viscosity After Storage (cS at 25° C.) |
| Example 18 | 0.58 | 66.5 | 55 | R.T.* | 68.5 |
| " | 0.58 | 66.5 | 55 | 50 | 74.5 |
| Example 19 | 0.09 | 66.5 | 55 | R.T. | 69.4 |
| " | 0.09 | 66.5 | 55 | 50 | 85.7 |
| (Comparative) Example 20 | 0 | 66.5 | 53 | R.T. | 83.8 |
| (Comparative) Example 20 | 0 | 66.5 | 15 | 50 | Gel |

*R.T. (room temperature) was about 23° C.

From table 3 it can be seen that improved stability, as indicated by retention of initial viscosity, resulted when

Polydimethylsiloxane A

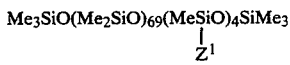
|
Z¹ in which Z₁ is —CH₂CH(Me)CH₂NC(O)CH=CH₂ ;
                                 |
                                 CH₂CH₂NC(O)CH=CH₂
                                 H

Polydimethylsiloxane B

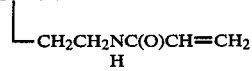

in which Z₂ is —CH₂CH(Me)CH₂NC(O)CH=CH₂.
                                  |
                                  Me These polydimethylsiloxanes were evaluated for thermal stability at 132° C. ±/−2° C. according to the method described in Examples 1–4, above. These polymer fluids were mixed with the indicated quantities of diethylhydroxylamine (see Table 4) and similarly tested for stability.

TABLE 4
Stability of Acrylamide Functional Polydimethylsiloxanes

| Example | Polydimethylsiloxane | Parts Diethyl-hydroxylamine per 100 Parts Polydimethylsiloxane | Gel Time at 132° C. +/− 2° C. |
| --- | --- | --- | --- |
| Example 25 (Comparative) | A | 0.062 | between 6 and 7.6 hours |
| Example 26 | A | 0 | 1.7 hours |
| Example 27 (Comparative) | B | 0.099 | between 4 and 6 hours |
| Example 28 | B | 0 | <1 hour |

From Table 4 it can be seen that the compositions which contained the diethylhydroxylamine showed greater thermal stability than the control polydimethylsiloxanes. When structures similar to Polydimethylsiloxane B having higher degrees of polymerization (e.g.. about 98 dimethylsiloxane units) were tested it was found that addition of the diethylhydroxylamine did not improve stability at 132° C.

We claim:

1. A method for stabilizing an organosilicone selected from organopolysiloxanes having a reactive organic group bearing at least one radical selected from the group consisting of acryloxy, methacryloxy, acrylamide, methacrylamide, styryl and vinylbenzyl radicals, said method comprising adding to said organosilicone a stabilizing amount of a hydroxylamine compound selected from the group consisting of those having the general formula $Q_2NOH$ in which Q independently denotes an alkyl radical having 1 to 12 carbon atoms, a cycloalkyl group having 5 to 12 carbon atoms or an aryl group having 6 to 9 carbon atoms, and those having the formula

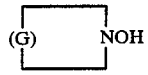

in which G denotes a hydrocarbyl group having 5 to 11 carbon atoms.

2. The method of claim 1, wherein said organosilicone is an organopolysiloxane comprising a plurality of independently selected units of the formula

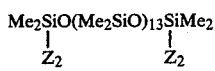

wherein Z is a reactive organic group bearing at least one radical selected from the group consisting of acryloxy, methacryloxy, acrylamide, methacrylamide, styryl and vinylbenzyl radicals, R' is independently selected from the group consisting of alkyl radicals having 1–6 carbon atoms, monovalent cycloaliphatic radicals, aryl groups, monovalent halohydrocarbyl groups having 1 to 6 carbon atoms and monovalent haloaromatic groups, c is 0, 1, 2 or 3, d is 0, 1 or 2 and the sum (c+d) is less than 4.

3. The method of claim 2, where in said hydroxylamine compound is selected from the group consisting of diethylhydroxylamine and dibenzylhydroxylamine.

4. The method of claim 2, wherein Z is a reactive organic group bearing at least one radical selected from the group consisting of acryloxy, methacryloxy, acrylamide and methacrylamide radicals.

5. The method of claim 4, wherein said organopolysiloxane is selected from the group consisting of those having average structures which may be represented by the formulae

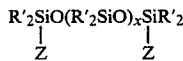

and

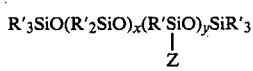

wherein x is 0 to about 100 and y is 1, to about 30.

6. The method of claim 5, wherein R' is selected from the group consisting of methyl, phenyl and trifuoropropyl radicals.

7. The method of claim 6, wherein said hydroxylamine compound is diethylhydroxylamine.

8. The method of claim 7, wherein R' is methyl, x is less than about 70, y iss 1 to 4 and Z is selected from the group consisting of the structures.

$$-CH_2CH_2CH_2\underset{H}{N}C(O)CH=CH_2$$

$$-CH_2CH(Me)CH_2\underset{Me}{N}C(O)CH=CH_2 \quad \text{and}$$

$$-CH_2CH(Me)CH_2\underset{\underset{H}{|}-CH_2CH_2NC(O)CH=CH_2}{N}C(O)CH=CH_2$$

in which Me denotes a methyl radical.

9. The method of claim 6, wherein said hydroxylamine compound is dibenzylhydroxylamine.

10. A composition comprising an organosilicone selected from organopolysiloxanes having a reactive organic group bearing at least one radical selected from the group consisting of acryloxy, methacryloxy, acrylamide, methacrylamide, styryl and vinylbenzyl radicals; and a tabilizing amount of a hydroxylamine compound selected from the group consisting of those having the general formula $$Q_2NOH$$

in which Q independently denotes an alkyl radicals having 1 to 12 carbon atoms, a cycloalkyl group having 5 to 12 carbon atoms or an aryl group having 6 to 9 carbon atoms, and those having the formula

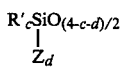

in which G denotes a hydrocarbyl group having 5 to 11 carbon atoms.

11. The composition of claim 10, where in said organosilicone is an organopolysiloxane comprising a plurality of independently selected units of the formula $$R'_cSiO_{(4-c-d)/2}$$
$$|$$
$$Z_d$$

wherein Z is a reactive organic group bearing at least one radical selected from the group consisting of acryloxy, methacryloxy, acrylamide, methacrylamide, styryl and vinylbenzyl radicals, R' is indepeddently selected from the group consisting of alkyl radicals having 1-6 carbon atoms, monovalent cycloaliphatic radicals, aryl groups, monovalent halohydrocarbyl groups having 1 to 6 carbon atoms and monovalent haloaromatic groups, c is 0, 1, 2 or 3, d is 0, 1 or 2 and the sum (c+d) is less than 4.

12. The composition of claim 11, wherein said hydroxylamine compound is selected from the group consisting of diethylhydroxylamine and dibenzylhydroxylamine.

13. The composition of claim 11, wherein Z is a reactive organic group bearing at least one radical selected from the group consisting of acryloxy, methacryloxy, acrylamide and methacrylamide radicals.

14. The composition of claim 13, wherein said organopolysiloxane is selected from the group consisting of those having average structures which may be represented by the formulae $$R'_2\underset{Z}{Si}O(R'_2SiO)_x\underset{Z}{Si}R'_2$$

and $$R'_3SiO(R'_2SiO)_x(R'SiO)_y\underset{Z}{SiR'_3}$$

wherein x is 0 to about 100 and y is 1 to about 30.

15. The composition of claim 14, wherein R' is selected from the group consisting of methyl, phenyl and trifuoropropyl radicals.

16. The composition of claim 15, wherein said hydroxylamine compound is diethylhydroxylamine.

17. The composition of claim 16, wherein R' is methyl, x is less than about 70, y is 1 to 4 and Z is selected from the group consisting of the structures.

$$-CH_2CH_2CH_2\underset{H}{N}C(O)CH=CH_2$$

$$-CH_2CH(Me)CH_2\underset{Me}{N}C(O)CH=CH_2$$

and $$-CH_2CH(Me)CH_2\underset{\underset{H}{|}-CH_2CH_2NC(O)CH=CH_2}{N}C(O)CH=CH_2 \quad ,$$

in which Me denotes a methyl radical.

18. The composition of claim 15, wherein said hydroxylamine compound is dibenzylhydroxylamine.

19. The composition of claim 11, further comprising a stabilizer for said organosilicone selected from the group consisting of monomethylether of hydroquinone, 4-tertbutylcatechol, 2,6-dibutyl-4-methylphenol, hydroquinone and phenothiazine.

* * * * *